US008246868B2

(12) United States Patent
Ichikawa et al.

(10) Patent No.: US 8,246,868 B2
(45) Date of Patent: Aug. 21, 2012

(54) METHOD FOR PRODUCING VESICLE, VESICLE OBTAINED BY THE PRODUCTION METHOD, AND METHOD FOR PRODUCING FROZEN PARTICLE USED IN PRODUCTION OF VESICLE

(75) Inventors: Sosaku Ichikawa, Ibaraki (JP); Takashi Kuroiwa, Tokyo (JP)

(73) Assignee: University of Tsukuba, Ibaraki (JP)

( * ) Notice: Subject to any disclaimer, the term of this patent is extended or adjusted under 35 U.S.C. 154(b) by 279 days.

(21) Appl. No.: 12/449,882

(22) PCT Filed: Mar. 3, 2008

(86) PCT No.: PCT/JP2008/053740
§ 371 (c)(1),
(2), (4) Date: Oct. 2, 2009

(87) PCT Pub. No.: WO2008/108324
PCT Pub. Date: Sep. 12, 2008

(65) Prior Publication Data
US 2010/0029791 A1 Feb. 4, 2010

(30) Foreign Application Priority Data
Mar. 2, 2007 (JP) ................................. 2007-053089

(51) Int. Cl.
*B01F 3/08* (2006.01)
*B01J 3/08* (2006.01)
(52) U.S. Cl. ............ 264/4; 264/4.1; 264/4.3; 264/4.32; 264/4.33; 264/4.6; 264/4.7; 427/213.3; 427/213.31; 427/213.32; 427/213.33; 427/213.34; 427/213.35; 427/213.36; 428/402; 428/402.2; 428/402.21; 428/402.22; 428/402.24

(58) Field of Classification Search ............... 264/4–4.7; 427/213.3–213.36; 428/402–402.24
See application file for complete search history.

(56) References Cited

U.S. PATENT DOCUMENTS
5,902,842 A * 5/1999 Balderson et al. ............ 523/337
(Continued)

FOREIGN PATENT DOCUMENTS
EP 02115257 * 9/1986
(Continued)

OTHER PUBLICATIONS
Wick et al.: Chemistry & Biology; Apr. 1996, vol. 3: 277-285.
(Continued)

*Primary Examiner* — Irina S Zemel
(74) *Attorney, Agent, or Firm* — Carrier Blackman & Associates, P.C.; William D. Blackman

(57) ABSTRACT

A W/O emulsion is produced from an aqueous solution containing a substance to be entrapped in a vesicle in a dissolved or suspended state and an oil phase containing an emulsifier; subsequently, the W/O emulsion is cooled to a temperature at which the aqueous solution of the W/O emulsion becomes a frozen particle and the oil phase maintains a liquid state, and the oil phase is removed; thereafter, an oil phase containing a vesicle constituent lipid is added to the frozen particle, and the obtained mixture is then stirred, so as to substitute the emulsifier on the surface of the frozen particle with the vesicle constituent lipid; and thereafter, an external Water phase is added to the frozen particle coated with a lipid membrane, so as to hydrate the lipid membrane by the external water phase. This process achieves a high entrapment yield of a desired substance while controlling desired physical properties such as particle diameter.

25 Claims, 9 Drawing Sheets

U.S. PATENT DOCUMENTS

2006/0121122 A1   6/2006   Nakajima et al.

FOREIGN PATENT DOCUMENTS

| JP | 2008-029952 | 2/2008 |
|---|---|---|
| WO | WO 2004/026457 | 4/2004 |

OTHER PUBLICATIONS

Szoka et al.: Proceedings of the National Academy of Sciences of the United States of America, Sep. 1978, vol. 75, No. 9, pp. 4194-4198.

* cited by examiner

Injection of dispersion phase solution via MC
(Deq: equivalent channel diameter)

Mean droplet diameter 7 μm    Mean droplet diameter 13 μm

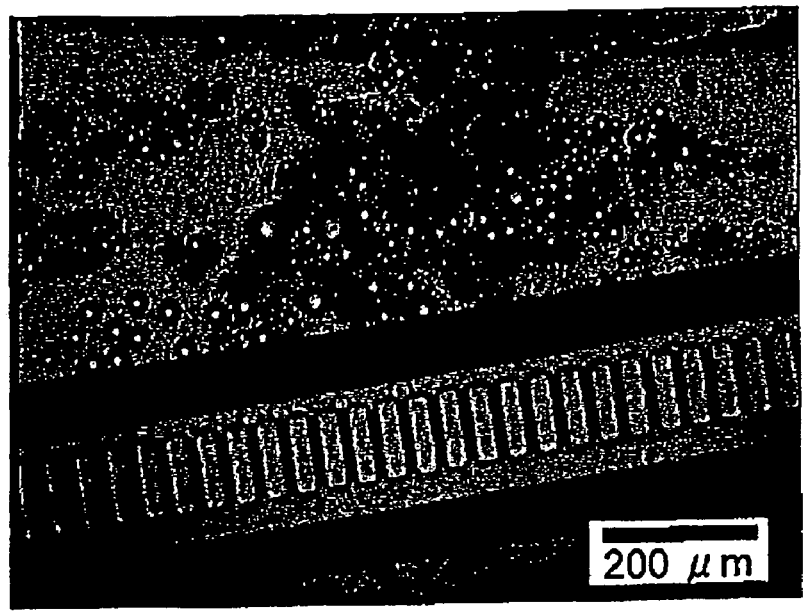
FIG. 10a  Phospholipid concentration
1.3 mM
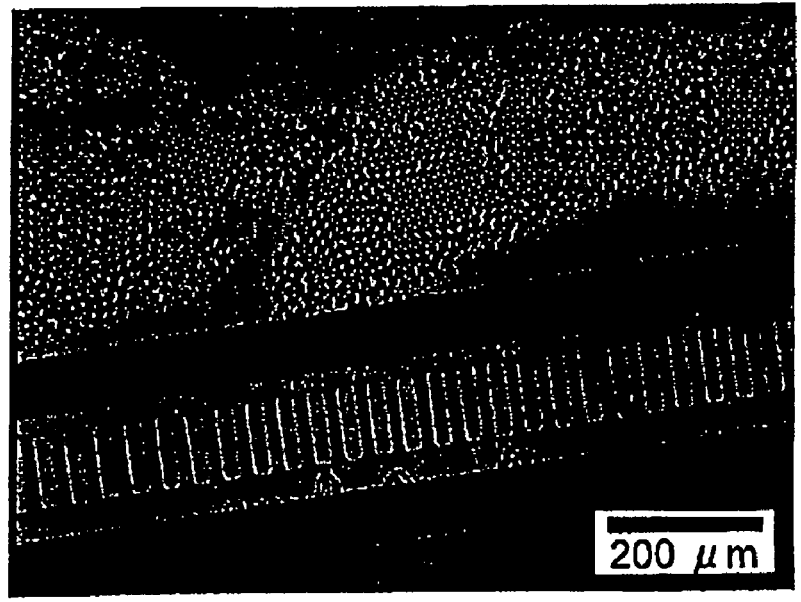
FIG. 10b  Phospholipid concentration
6.5 mM

METHOD FOR PRODUCING VESICLE, VESICLE OBTAINED BY THE PRODUCTION METHOD, AND METHOD FOR PRODUCING FROZEN PARTICLE USED IN PRODUCTION OF VESICLE

CROSS-REFERENCE TO RELATED APPLICATIONS

The present application is a U.S. National phase of, and claims priority based on PCT/JP2008/052925, filed 3 Mar. 2008, which, in turn, claims priority from Japanese patent application 2007-053089, filed 2 Mar. 2007. The entire disclosure of each of the referenced priority documents is incorporated herein by reference.

TECHNICAL FIELD

The present invention relates to a method for producing a vesicle, and particularly to a method for producing a vesicle having a mean particle diameter between several and several hundred of μm, which comprises a W/O emulsion as a substrate, and comprises various substances such as a water-soluble substance, a solid particle, or a cell in the internal water phase thereof (hereinafter referred to as "the vesicle of the present invention" at times).

BACKGROUND ART

A vesicle is also referred to as a liposome, and it is a small enclosed compartment formed by an amphiphilic lipid molecule. Thus, it is anticipated that such vesicle will be used for various purposes such as a model cell membrane, a DDS preparation and a microreactor for research usage.

An example of a method for producing a vesicle is a method comprising hydrating a thin lipid membrane formed on the surface of a solid. For example, a thin lipid membrane is formed on a glass substrate, and an aqueous solution is then added thereto, followed by intensive stirring, so as to prepare a vesicle. However, the particle diameters of vesicles obtained by this method are generally non-uniform, and the efficiency of entrapping a desired substance in the vesicle is extremely low. Moreover, it is difficult for this method to prepare a large vesicle having a particle diameter of a micrometer-scale.

On the other hand, as a method that has been frequently used in the production of a large vesicle, an electroformation method disclosed in Non-Patent Document 1 is known. This method comprises applying an electric voltage to a thin lipid membrane formed on a platinum electrode in an aqueous solution to hydrate the thin lipid membrane, so as to produce a vesicle with a diameter between approximately several tens of and several hundreds of μm.

Moreover, as a method for producing a vesicle having a relatively high entrapment yield, a method using emulsion is proposed in Non-Patent Document 2.

Herein, the term "entrapped substance" is used in the present invention to mean a substance entrapped in a vesicle. The term "entrapment yield" is used herein to mean the ratio of substances entrapped in a vesicle to those contained in the finally obtained vesicle suspension as a whole. Furthermore, the term "mean particle diameter" is used herein to mean a particle diameter calculated as a geometric mean of number reference in the number distribution of vesicle particle diameters.

Further, Patent Document 1 proposes a method for producing a microcapsule, which comprises forming a gel layer of an electrolytic complex around a polyelectrolyte solution. In this method, a polyelectrolyte solution (a dispersion phase) in which a given substance is entrapped is disposed on one side of a microchannel, and a solution (a continuous phase) that reacts with the polyelectrolyte solution to form a gel is disposed on the other side thereof. By applying pressure to the dispersion phase, the dispersion phase is supplied as fine particles to the continuous phase, so that a gel layer is formed by a reaction occurring on the surface of the dispersion phase.
Patent Document 1: WO 2004/026457
Non-Patent Document 1: Wick et al.: Chemistry & Biology, Vol. 3, 277-285, 1996
Non-Patent Document 2: Szoka et al.: Proc. Natl. Acad. Sci. USA, Vol. 75, No. 9, 4194-4198, 1978

DISCLOSURE OF THE INVENTION

Problems to be Solved by the Invention

In the case of the method disclosed in Non-Patent Document 1, in order to entrap a substance in the internal water phase of the obtained vesicle, it is necessary to carry out an operation to inject such substances into individual vesicles using special equipment such as a microinjection system. Thus, the mass production of such vesicles cannot be anticipated.

In the case of the production technique using emulsion disclosed in Non-Patent Document 2, it is difficult to control the size of an obtained vesicle, and it is particularly difficult to produce a large vesicle of a size of more than 10 μm. In other previously reported techniques, the entrapment efficiency of a substance in a vesicle is generally between approximately several percent and several tens of percent. Thus, these techniques could not simultaneously achieve both the control of particle diameter and high entrapment yield.

According to the method disclosed in Patent Document 1, uniform microcapsules having a particle diameter of several hundreds of μm, in which given substances are entrapped, are obtained. However, in this method, the type of an aqueous solution in which a given substance is dissolved or entrapped is limited to a specific polyelectrolyte solution such as an alginic acid aqueous solution. In addition, this method is also problematic in that a gel layer formed by the reaction is fragile.

Means for Solving the Problems

In order to solve the aforementioned problems, in the method for producing a vesicle according to a first aspect of the present invention, a W/O emulsion is produced from an aqueous solution containing a substance to be entrapped in a vesicle in a dissolved or suspended state and an oil phase containing an emulsifier; subsequently, the W/O emulsion is cooled to a temperature at which the aqueous solution of the W/O emulsion becomes a frozen particle and the oil phase maintains a liquid state, and the oil phase is removed; thereafter, an oil phase containing a vesicle constituent lipid is added to the frozen particle, and the obtained mixture is then stirred, so as to substitute the emulsifier on the surface of the frozen particle with the vesicle constituent lipid; and thereafter, an external water phase is added to the frozen particle coated with a lipid membrane, so as to hydrate the lipid membrane by the external water phase.

According to a second aspect of the present invention of the present application, a substance capable of constituting a vesicle is particularly selected as an emulsifier, so as to omit the step of substituting the emulsifier with a vesicle constituent substance.

Specifically, a W/O emulsion is produced from an aqueous solution containing a substance to be entrapped in a vesicle in a dissolved or suspended state and an oil phase containing a lipid that functions an emulsifier (phosphatidyl choline, sorbitan fatty acid ester, etc.); subsequently, the W/O emulsion is cooled to a temperature at which the aqueous solution of the W/O emulsion becomes a frozen particle coated with a lipid membrane and the oil phase maintains a liquid state, and the oil phase is removed; and thereafter, an external water phase is added to the frozen particle, so as to hydrate the external water phase and the lipid membrane on the surface of the frozen particle.

It is preferable to mix a fine vesicle made of the same type of lipid membrane, when the external water phase is added to the frozen particle. It was revealed that, by mixing a fine vesicle made of the same type of lipid membrane, the lipid membrane on the fine vesicle repairs damage formed on the lipid membrane on the surface of a vesicle with a large particle diameter.

Moreover, when an external water phase is added to the frozen particle, by adding a substance for lowering the freezing point of the external water, such as glycerol, together with the external water phase, the lipid membrane can be hydrated, for example, while keeping the frozen particle in the frozen state at −2° C., so as to improve entrapment yield.

Furthermore, when the oil phase is removed by evaporation under reduced pressure, it is preferable that the inside of a vessel used have been hydrophobized. By hydrophobizing the inside of the vessel, the inner surface of the vessel is not allowed to directly come into contact with the frozen particle, a lipid layer is formed between them, and the particle does not break until completion of hydration, while maintaining a round shape. Thus, entrapment yield is increased.

Still further, the invention of the present application includes a vesicle obtained by the aforementioned methods, and also includes a method for producing a frozen particle that is an intermediate product before processing into the vesicle.

Advantages of the Invention

According to the present invention, it is possible to produce a vesicle, which achieves a high entrapment yield of a desired substance while controlling desired physical properties such as particle diameter. In addition, it is also possible to produce a vesicle having a sufficient strength (shape-maintaining ability) necessary for a model cell membrane, a DDS preparation and a microreactor for research usage. Specific effects of the present invention are as follows, for example.

(1) It is possible to provide a vesicle having a controlled particle diameter (micrometer order size), the production of which has previously been difficult. In addition, it is possible to produce a vesicle having a desired mean particle size within the range between approximately 0.03 and 200 μm.

(2) It is possible to encapsulate a substance in the internal water phase of a vesicle having a controlled particle diameter at a high entrapment yield. In particular, it is possible to provide simultaneously, and relatively in large quantities, water-soluble-substance-entrapped giant vesicles, which have been produced individually under a microscope by the prior art techniques.

(3) By changing the kind of an amphiphilic lipid dissolved in the oil phase of a W/O emulsion, vesicles having various lipid compositions can be relatively easily produced.

(4) As long as it is a substance that can be dissolved or dispersed in the disperse water phase of a W/O emulsion, it can be entrapped in a vesicle, regardless of the type of the entrapped substance. Accordingly, a vesicle produced by the present invention can be used as a carrier of hydrophilic and hydrophobic drugs in DDS. Moreover, such vesicle can also be used as a microreactor, in which a reaction relating to a gene or a protein is carried out, in the screening of a useful gene or protein.

(5) Since agents used in the production process of a vesicle are all highly safe and can be used even for food application, a vesicle produced by the present invention is anticipated to be highly safe. Accordingly, the vesicle of the present invention is preferable as a carrier used for drugs, functional food ingredients, and cosmetic ingredients. The vesicle of the present invention can be applied, for example, to the production of functional food capsules capable of suppressing oxidation of various types of vitamins, or the production of cosmetic solutions having high moisturizing effects and the like, utilizing vesicles in which moisturizing ingredients are entrapped.

BRIEF DESCRIPTION OF THE DRAWINGS

FIGS. 10(a) and (b) are views showing the influence of lipid concentration on the uniformity of a W/O emulsion.

BEST MODE FOR CARRYING OUT THE INVENTION

FIGS. 1 (a) to (d) are views showing the outline of the process of producing a vesicle of the present invention. It is to be noted that enlarged portions on the right side are magnified views showing the main parts of the views on the left side. In the present invention, as shown in FIG. 1(a), W/O emulsion is first produced from a water phase containing an entrapped substance and an oil phase such as hexane.

Figure 1A:
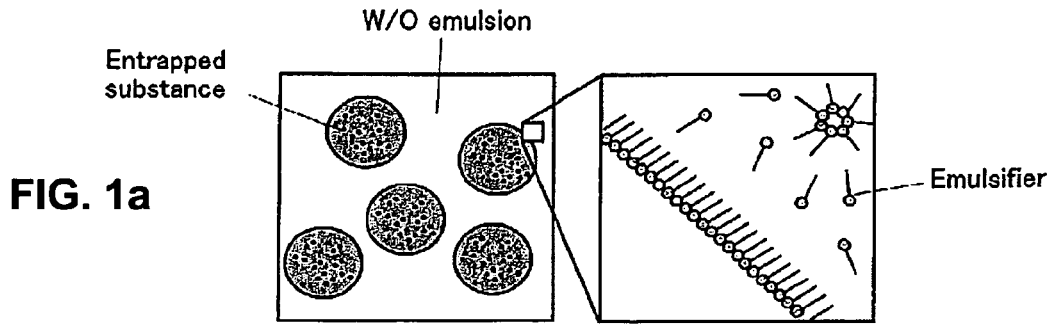
FIGS. 1(a) to (d) are views showing the outline of a process of producing a vesicle according to an exemplary embodiment of the present invention.
Figure 1B:
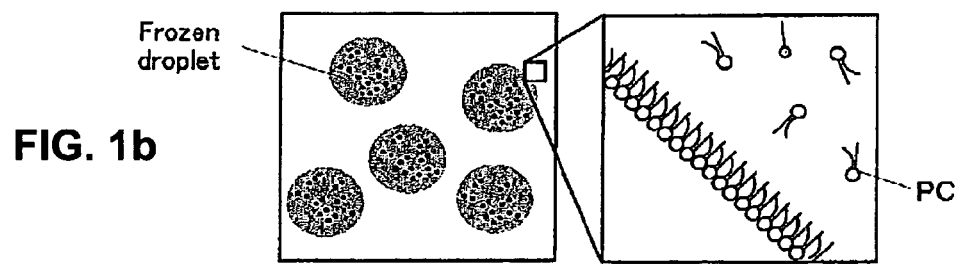

Subsequently, such W/O emulsion is frozen, and as shown in FIG. 1(b), an emulsifier on the surface of the frozen droplet is removed by washing, and at the same time, a vesicle constituent lipid (PC) is added thereto, so as to substitute the emulsifier with the vesicle constituent lipid.

Figure 1C:
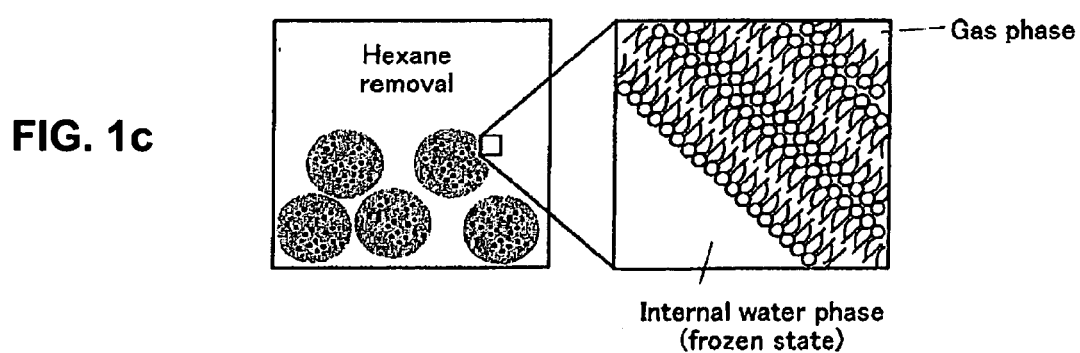
Figure 1D:
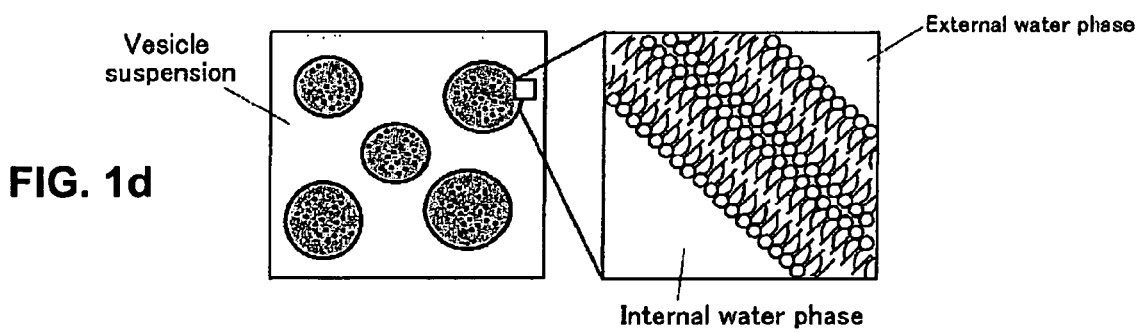

Thereafter, as shown in FIG. 1(c), the oil phase (hexane) is removed. At this point, a lipid bilayer membrane is formed on the surface of the frozen droplet. Thereafter, as shown in FIG. 1(d), an external water phase is added thereto to prepare a vesicle suspension.

Herein, the vesicle of the present invention includes not only a vesicle composed of a lipid bilayer membrane, but also a particle having a microcapsule structure, which comprises, as a wall material, a lipid species constituting a vesicle.

A lipid species (vesicle constituent lipid) that constitutes the vesicle of the present invention may not be limited, as long as it is an amphiphilic lipid molecule. Thus, the vesicle of the present invention also includes vesicles comprising, as constituents, phospholipids such as phosphatidyl choline, phosphatidyl glycerol, phosphatidyl inositol, phosphatidic acid and phosphatidyl serine, sphingolipids, emulsifiers used in foods, such as sorbitan fatty acid ester and polyglycerin fatty acid ester, and fatty acids such as oleic acid.

In addition, the lipid bilayer membrane may further comprise other ingredients within a range in which such ingredients do not impair the advantages of the present invention. For example, sterols such as cholesterol and ergosterol, charged lipids such as stearylamine, long-chain fatty acids such as oleic acid, stearic acid and palmitic acid, and peptides and carbohydrates that are able to interact with the lipid bilayer membrane, may also be used in combination with the aforementioned constituents.

In order to obtain a vesicle having higher size uniformity, a microchannel emulsification method for producing a W/O emulsion having extremely high monodispersion ability disclosed in Patent Document 1 is most advantageous.

As a water phase of a W/O emulsion, pure water or a buffer solution containing salts may be used. Such water phase may comprise a substance to be entrapped in the internal water phase of a vesicle after the production of the vesicle. The type of such entrapped substance is not limited, as long as it is a substance that can be dissolved or suspended in a water phase and does not impair the production of a W/O emulsion. Thus, low molecular weight substances such as sugars or salts, high molecular weight substances such as enzyme or DNA, and solid substances such as fine gel particles or fine magnetic particles may also be used as entrapped substances in the present invention.

As an oil phase of a W/O emulsion, an organic solvent that is immiscible with water, such as hexane, may be used. Such oil phase may comprise an emulsifier and a stabilizer, which can be used in the production of an emulsion according to a microchannel emulsification method. Examples of an available emulsifier include a phospholipid, a sorbitan fatty acid ester, a polyglycerin fatty acid ester, and a sucrose ester. Examples of an available stabilizer include fatty acids such as oleic acid and charged lipids such as stearylamine.

When a W/O emulsion is produced by a microchannel emulsification method, the following components are used: (a) a hydrophobized silicon microchannel substrate or acrylic microchannel plate; (b) a hydrophobized glass plate or acrylic plate; and a microchannel emulsifying apparatus module.

The aforementioned oil phase is filled on the outlet side of a grooved-type microchannel formed with (a) and (b) or a through-hole type microchannel formed on (a). Thereafter, by injecting the aforementioned water phase containing an entrapped substance from the inlet side of the microchannel, W/O emulsion having a uniform diameter, in which deviation in particle diameter is 10% or less, can be produced.

As a microchannel substrate, various shapes of substrates such as a dead-end type microchannel, a cross-flow type microchannel, and a straight-through-type microchannel, may be used. In a case in which strict control of particle diameter is not required, and in a case in which it is desired to produce an extremely small vesicle, it may also be possible to produce such vesicle in the following steps, utilizing a W/O emulsion obtained by a known membrane emulsification method, an ultrasonic emulsification method, and the use of a high pressure homogenizer.

In order to prevent droplets in the water phase from unification, the produced W/O emulsion is immediately frozen in liquid nitrogen, and the frozen W/O emulsion is preserved in a low-temperature environment in a state in which "the water phase becomes a solid (ice) and the oil phase remains as a liquid". For precipitation, the water phase is left at rest at the same temperature, and the oil phase as a supernatant is then removed by suction.

Subsequently, an oil phase containing a vesicle constituent lipid such as phosphatidyl choline is added to the remaining emulsion, and the suspension as a whole is then fully stirred. The same operation is repeated, until the originally contained emulsifier has been diluted to have a desired concentration. As a result, the emulsifier contained in the reaction system is substituted with the vesicle constituent lipid. At this time, by properly adjusting the ratio of the amount of the vesicle constituent lipid to the amount of the water phase droplets, the lamellarity of the lipid bilayer membrane of a vesicle to be produced later and the entrapment yield of the entrapped substance can be regulated.

The oil phase solvent is removed from the W/O emulsion, in which the emulsifier is substituted with the vesicle constituent lipid, by evaporation using an evaporator under reduced pressure, while the water phase is kept frozen. At this time, if the inner wall of a vessel containing the W/O emulsion is hydrophobic during the reduced-pressure evaporation operation, the entrapment yield of a substance entrapped in a vesicle to be produced later can be increased (please refer to the example section of the present specification). As such hydrophobic inner wall material, a glass vessel whose surface has been hydrophobized with a silane coupling agent such as octadecyltriethoxysilane, or a water repellent vessel made of fluorocarbon resin, can be used.

By removing the oil phase solvent from the W/O emulsion, a water phase droplet coated with the vesicle constituent lipid can be obtained. By adding an external water phase to this water phase droplet, the layer of the vesicle constituent lipid that covers the water phase droplet can be hydrated, thereby obtaining a vesicle.

Figure 2A:
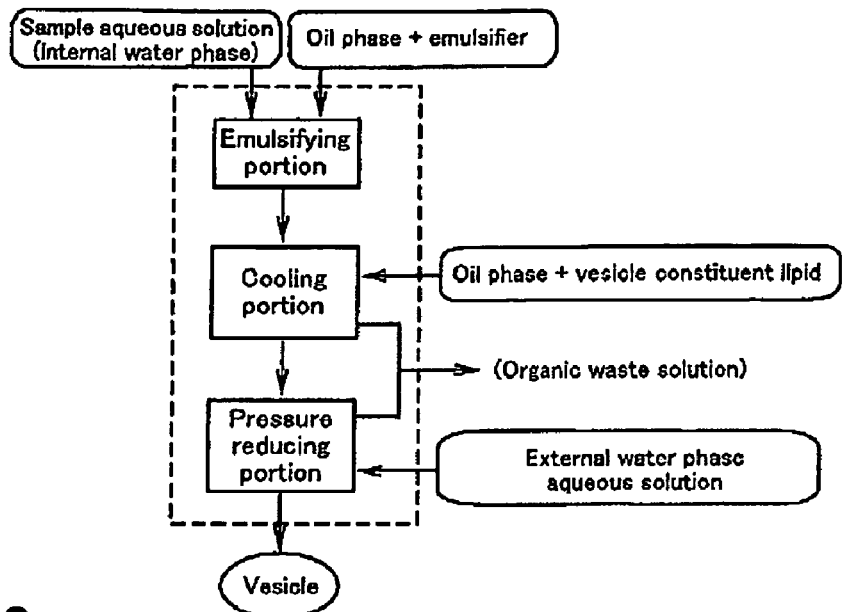
FIG. 2(a) is a view showing the flow of an apparatus according to an exemplary embodiment of the present invention, and (b) is a view showing a structural example of the apparatus.
Figure 2B:
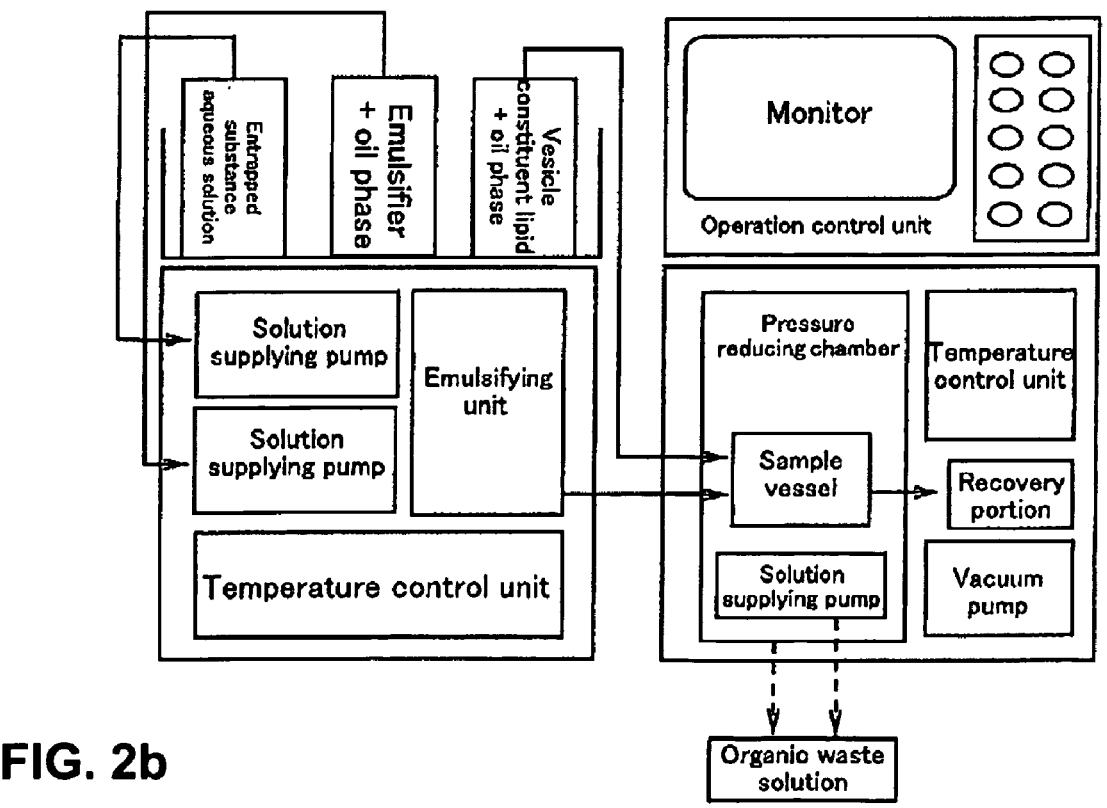

By integrating the aforementioned steps, there can be produced an apparatus for semi-automatically producing a vesicle only by introducing various ingredients therein. FIG. 2(a) shows the flow of such apparatus, and FIG. 2(b) shows a structural example of the apparatus.

The composition of an aqueous solution used as an external water phase is not limited, as long as it does not impair hydration of the vesicle constituent lipid layer and formation of a vesicle. If a nonfreezing aqueous solution, to which approximately 10% glycerol and the like have been added, and a phospholipid vesicle suspension having a particle diameter of approximately 50 nm are used, the entrapment yield of the entrapped substance can be enhanced.

It has been difficult for prior art techniques to efficiently entrap a substance in a vesicle of a micrometer-scale and also to produce a large number of uniform vesicles. However, according to the technique of the present invention, a large number of micrometer-scale vesicles, in which desired substances are entrapped at an entrapment yield of approximately several tens of percent, can be simultaneously obtained.

Thereby, the efficiency of a biochemical reaction or the like using such vesicle can be anticipated. That is to say, such reaction can be carried out inside the vesicle by a method comprising producing a vesicle containing reaction material A by the technique of the present invention and then supplying reaction material B reacting with the reaction material A from outside the vesicle via membrane permeation, or by a method comprising producing a vesicle containing the reaction material A and a vesicle containing the reaction material B by the technique of the present invention, and then fusing these vesicles. For example, if a substance that emits fluorescence when a reaction occurs is used as a reaction ingredient, fluorescence is observed inside the vesicle after the reaction has progressed.

The vesicle obtained by the present invention has a size of micrometer-scale. Thus, if an apparatus used for selection of cells, such as a cell sorter, is used, a vesicle that emits fluorescence after the reaction has progressed can easily be selected and fractionated from a vesicle in which the reaction has not progressed. By such principle, it becomes possible to screen for a useful enzyme, antibody, nucleic acid, etc.

Hereinafter, specific examples will be described.

Example 1

(Vesicle Constituent Lipid)

A mixture of phosphatidyl choline (hereinafter referred to as PC) as a neutral phospholipid, cholesterol (Chol) as a typical sterol, and stearylamine (SA) as a cationic lipid was used as a vesicle constituent lipid.

(Production of a W/O Emulsion with Uniform Diameter)

Hexane containing 3 wt % sorbitan monooleate (trade name: Span80) and 0.1 wt % SA was used as an oil phase, and a Tris-HCl buffer solution (pH 9) was used as a water phase. It was necessary to dissolve or disperse an entrapped substance in a water phase used in the production of a W/O emulsion. A fluorescent dye, calcein, was used as a model entrapped substance to be entrapped in a vesicle. Such calcein was dissolved in the water phase in a concentration of 0.4 mmol/L.

Figure 3A:
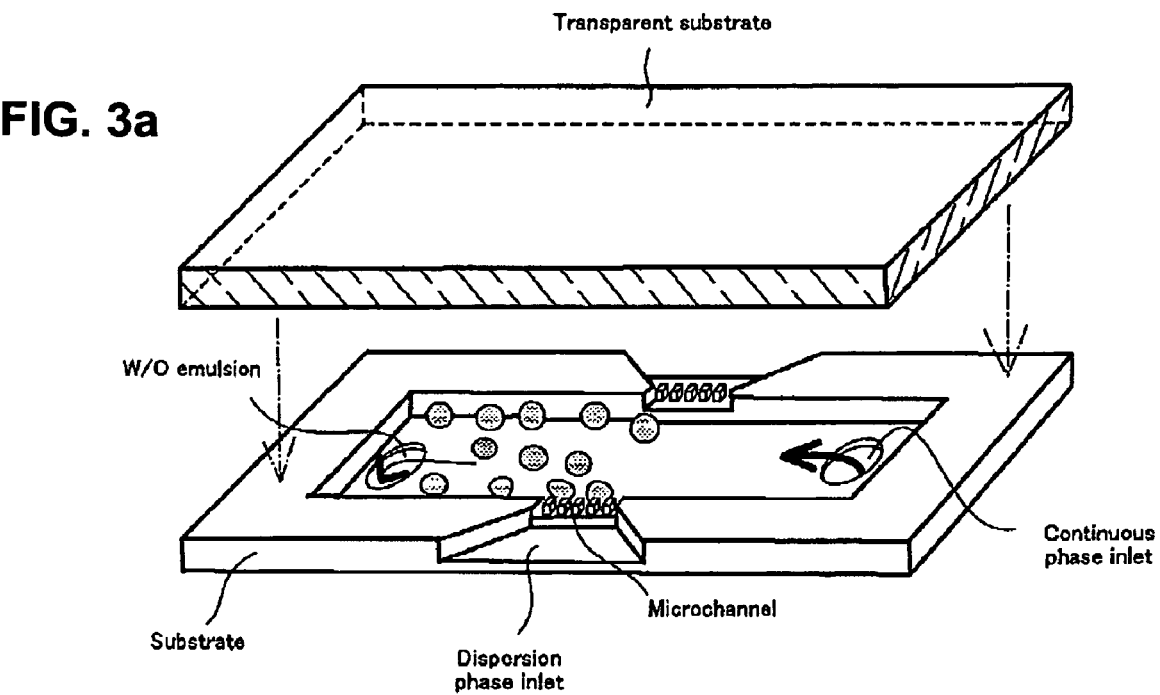
FIG. 3(a) is a perspective view of a cross-flow type microchannel emulsifying apparatus module according to an exemplary embodiment of the present invention, and (b) is a magnified view of the main part of the same module.
Figure 3B:
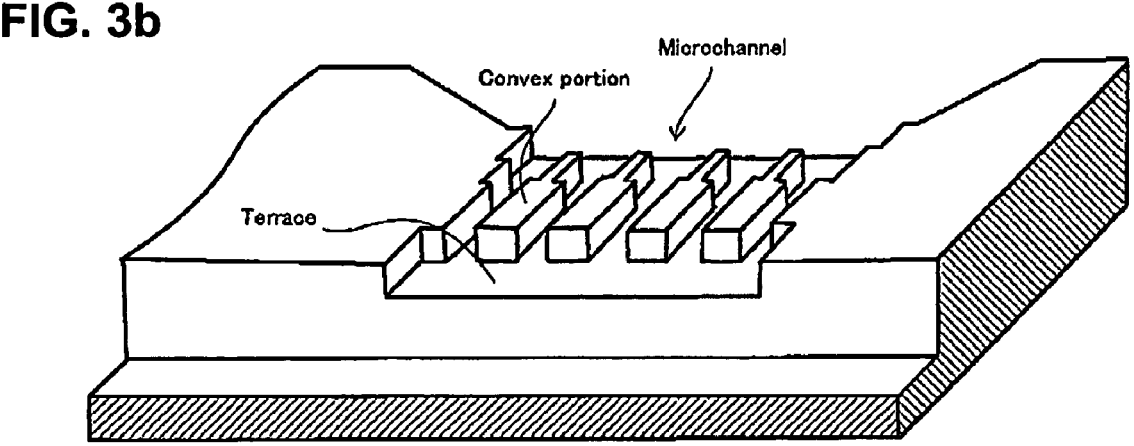

For the production of a W/O emulsion, a cross-flow type microchannel emulsifying apparatus module for experimental use, as shown in FIG. 3, was used. As a microchannel substrate, a microchannel substrate made of silicon, which had been hydrophobized with octadecyltriethoxysilane, was used.

The terrace length, channel depth, and channel width of the microchannel substrate were approximately 15 μm, 2 μm, and 5 μm, respectively. The microchannel substrate was press-fitted to a glass plate that had been subjected to a hydrophobization treatment with octadecyltriethoxysilane, and the hexane solution as an oil phase was then filled on the outlet side of the formed microchannel. Thereafter, the water phase was supplied from the inlet side of the channel, so as to produce a W/O emulsion with a uniform diameter.

Figure 4:
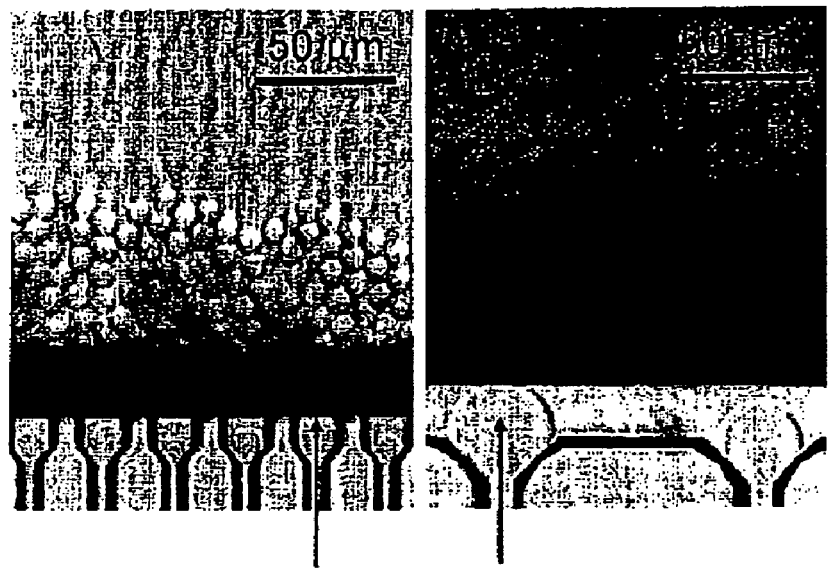
FIG. 4 shows microphotographs of the W/O emulsion of Example 1.
Figure 5:
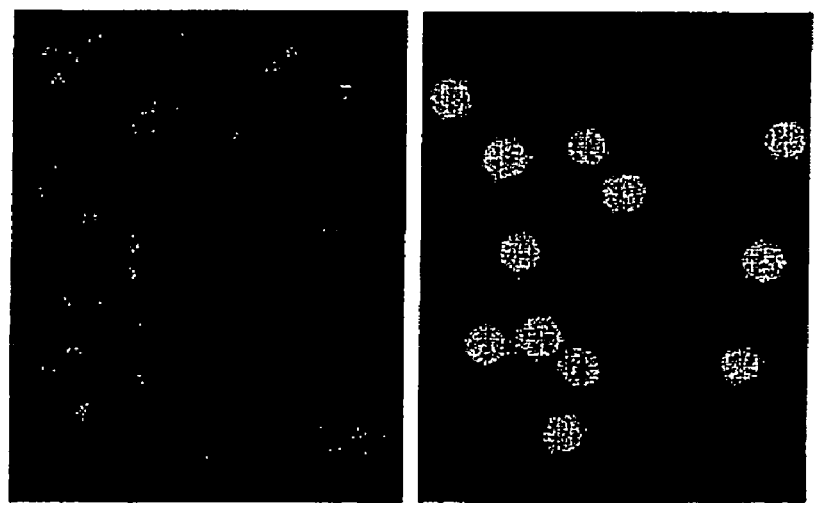
FIG. 5 shows microphotographs of a W/O emulsion, in which only droplets of the water phase emit fluorescence.

FIG. 4 shows microphotographs of the obtained W/O emulsion. The diameter of the obtained emulsion was almost uniform (4 to 6 μm). As a result of observation under a fluorescence microscope shown in FIG. 5, it was observed that only droplets in the water phase emitted fluorescence, and it was confirmed that the entrapped substance, calcein, was contained in the droplets in the water phase.

(Production of Calcein-Entrapped Vesicle)

The W/O emulsion obtained by the aforementioned method was frozen in liquid nitrogen, and it was then preserved in a low-temperature chamber at −10° C. By this treatment, emulsion in which the oil phase remained as a liquid and the water phase became a solid (ice) could be obtained. While keeping the temperature at −10° C., the emulsion was left at rest for 30 minutes, so that the water phase droplets were precipitated. Thereafter, 95% (volume ratio) of a supernatant (the oil phase) was removed by suction. The remaining emulsion was 20 times diluted with a hexane solution containing PC, Chol, and SA, and the diluted solution as a whole was then fully stirred. The molar ratio among PC, Chol, and SA was set at 5:5:1. The total lipid concentration was set at 1.6 g/L.

The emulsion was left at rest for 30 minutes again, and 90% of a supernatant was then removed. The remaining emulsion was 10 times diluted with a hexane solution containing the aforementioned vesicle constituent lipid, and the diluted emulsion as a whole was then stirred.

Thereafter, the emulsion was further left at rest for 30 minutes, so as to precipitate the water phase, and 60% of a supernatant was then removed. The residue was 2.5 times diluted with a hexane solution containing the aforementioned vesicle constituent lipid. The concentration of the water phase in the emulsion was adjusted, and the emulsion was then 2 times diluted with the same above hexane solution, so as to obtain W/O emulsion containing a water phase at a concentration of 10 mg/mL.

It was confirmed by high performance liquid chromatography that, by the aforementioned operation, Span80 used in the production of a W/O emulsion was diluted to a concentration of approximately 1/1,000, and that 95% or more of total lipids (including an emulsifier) contained in the emulsion were substituted with vesicle constituent lipids.

While keeping the temperature at −10° C., the W/O emulsion after the operation of emulsifier substitution was 10 times diluted with a hexane solution containing any given concentration of vesicle constituent lipid, so as to obtain W/O emulsion having a lipid concentration of 0.02 to 1.6 mg/mL and a water phase concentration of 1 mg/mL.

Figure 6:
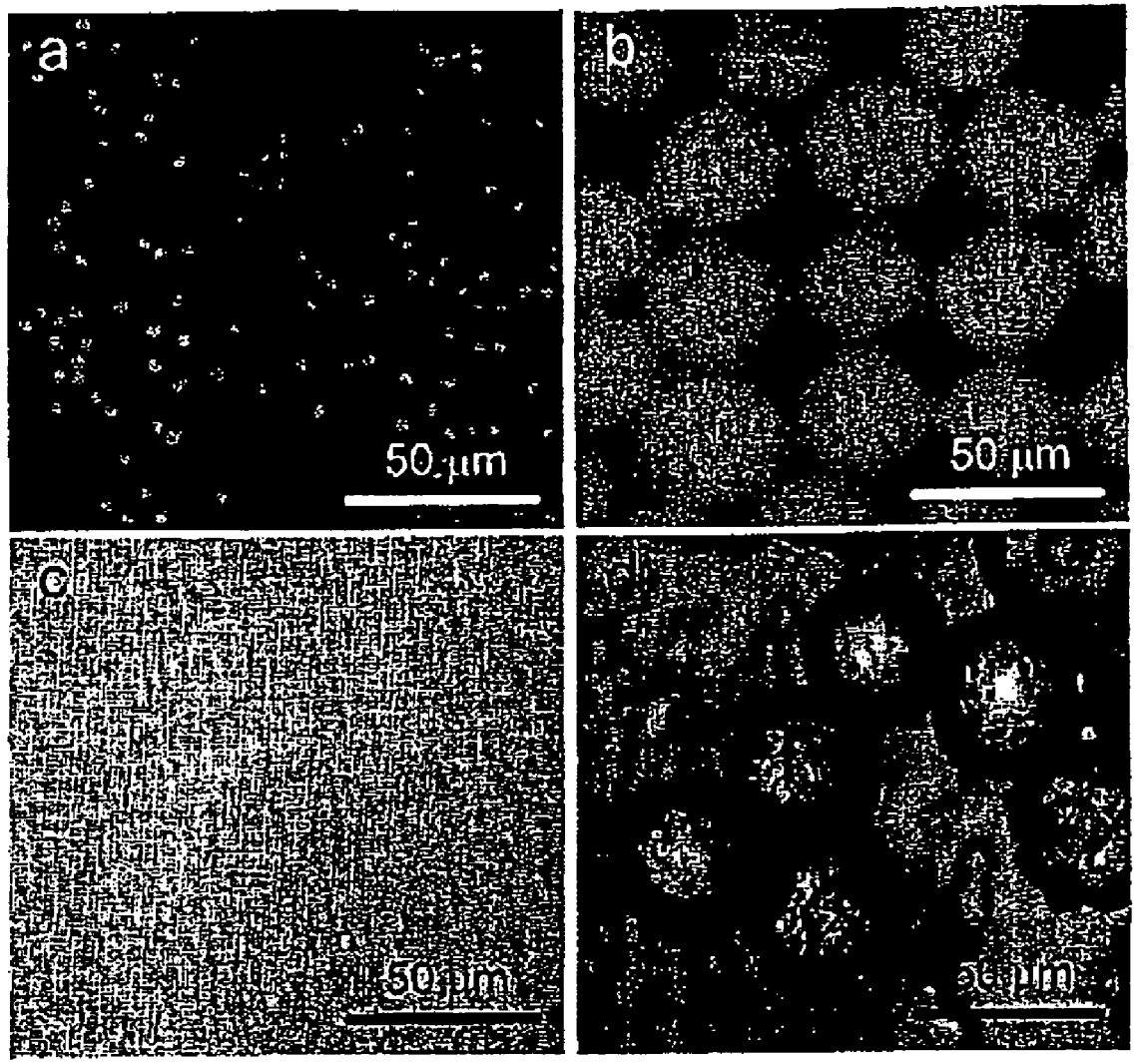
FIGS. 6(a) and (b) are microphotographs showing droplets before they have been frozen, and (c) and (d) are microphotographs showing the state of frozen droplets after they have been frozen and hexane has been removed by evaporation.

The hexane as an oil phase solvent contained in the obtained emulsion was evaporated and removed with a rotary evaporator under conditions of −5° C. to −10° C. and 15 to 20 hPa. FIGS. 6(a) and (b) are microphotographs showing the state of droplets before the freezing operation, and (c) and (d) are microphotographs showing the state of the frozen droplets after they have been frozen and hexane has been removed by evaporation. From these microphotographs, it is found that the frozen droplets maintained their shapes after the removal of the continuous phase.

Subsequently, 0.05 to 1 mL of a 50 mmol/L Tris-HCl buffer solution (pH 9) was added as an external water phase to the remaining emulsion at 4° C., so as to hydrate a thin lipid membrane that covered the frozen water phase droplet. The total amount of the resultant was diluted with the same above buffer solution at any given ratio, and the diluted solution was then left at rest at room temperature, so as to obtain a vesicle suspension.

Figure 7:
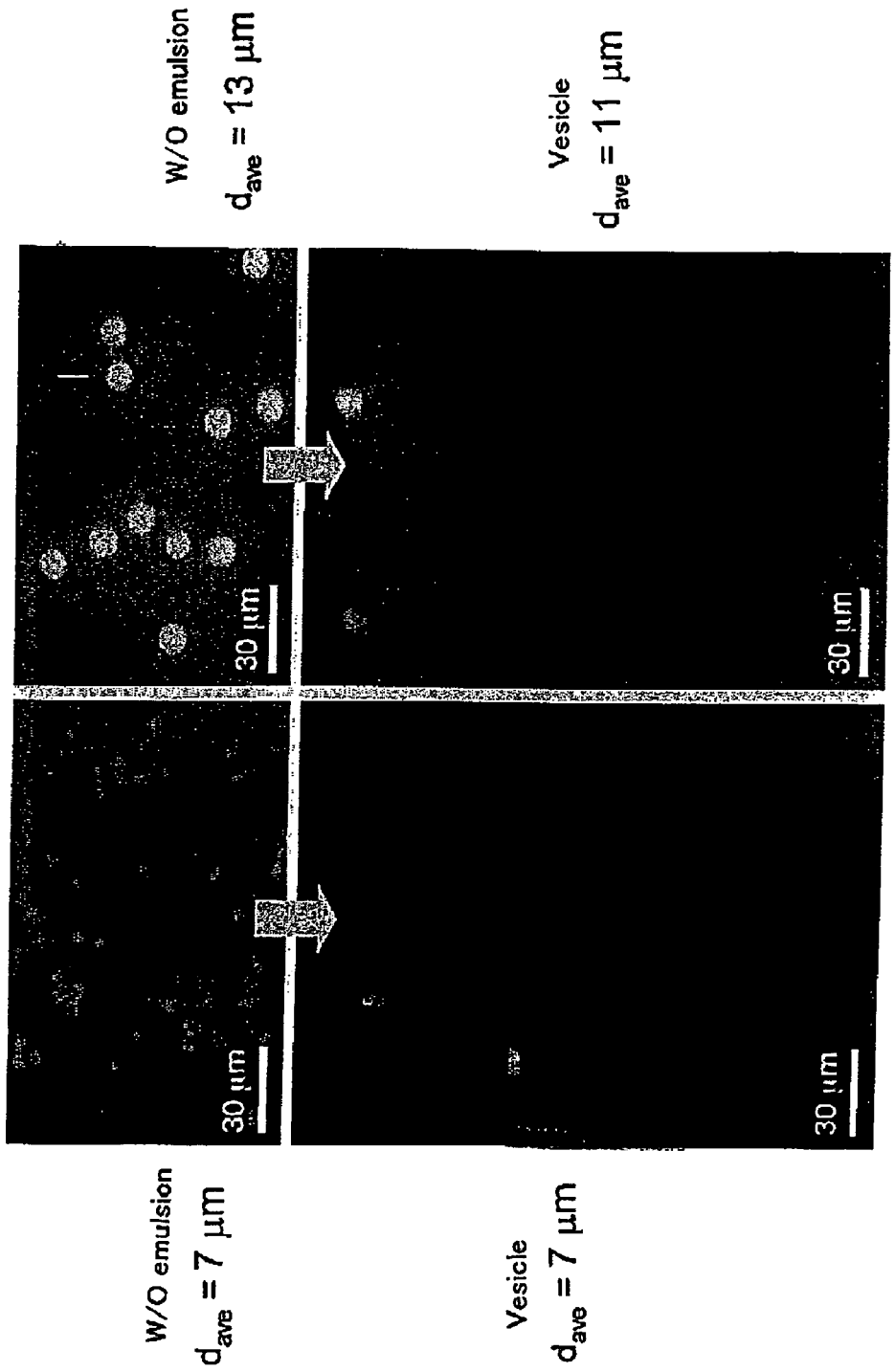
FIG. 7 show microphotographs of vesicles produced in Example 1.

The lower microphotographs of FIG. 7 show vesicles obtained in the present example. A majority of the obtained vesicles have a diameter between 1 and 10 μm. The size of the vesicles reflected the size of a W/O emulsion used as a substrate (upper microphotographs of FIG. 7). In addition, the fluorescence of calcein was observed inside such vesicle, and thus it was confirmed that calcein used as a substance to be entrapped was actually entrapped in the vesicle. The entrapment yield of calcein was measured by the method of Oku et al. (Oku et al.: Biochim. Biophys. Acta, vol. 691, 332-340, 1982). As a result, the entrapment yield was found to be approximately 12%.

Example 2

The procedures of Example 1 were modified to improve the entrapment yield of calcein. A 50-nm vesicle suspension consisting of 20 mmol/L PC and a 10 wt % glycerol solution were used as external water phases. In addition, as a vessel used during the removal of hexane by evaporation and hydration of a lipid membrane, a glass vessel whose surface had been hydrophobized was used.

(Production of 50-nm Vesicle Suspension)

Chloroform containing 2 wt % PC was placed in a glass vessel, and the chloroform was then removed by evaporation under reduced pressure, so as to form a thin membrane of PC on the bottom of the glass vessel. Thereafter, a Tris-HCl buffer solution (50 mmol/L, pH 9) was added thereto to a PC concentration of 20 mmol/L, and the obtained mixture was intensively shaken and stirred to hydrate the thin PC membrane, so as to obtain a multilayer vesicle suspension. This suspension was frozen in liquid nitrogen and was then melted in a room temperature water tank. This operation was repeated 5 times. The obtained suspension was forced to successively permeate through 400-, 200-, 100-, and 50-nm polycarbonate filters, 10 times each, thereby obtaining a vesicle suspension containing vesicles with a diameter of 50 nm.

(Production of 10 Wt % Glycerol Solution)

Glycerol was dissolved in a Tris-HCl buffer solution (50 mmol/L, pH 9) to a concentration of 10 wt %, so as to prepare a glycerol solution.

(Hydrophobization Treatment of Surface of Glass Vessel)

A Pyrex (registered trade mark) glass test tube was filled with toluene containing 5 wt % octadecyltriethoxysilane, and the inside of the test tube was subjected to a hydrophobization treatment in a 110° C. oil bath for 60 minutes under recirculation of toluene. After completion of the treatment, the test tube was washed with toluene, hexane, a 50% ethanol aqueous solution, and deionized water in this order.

(Improvement of Entrapment Yield by Modification of Process)

A W/O emulsion was prepared by a microchannel emulsification method in the same manner as that of Example 1. Substitution of an emulsifier and the removal of an oil phase solvent were then carried out by the same procedures. The subsequent hydration treatment of a thin lipid membrane was carried out by the following operations.

- Add a Tris-HCl buffer solution (50 mmol/L, pH 9) to hydrate the thin lipid membrane (=Example 1).
- Use the above described vesicle suspension with a diameter of 50 nm as an external water phase added to the reaction system, so as to hydrate the thin lipid membrane.
- Use a 10% glycerol solution at a temperature of −2° C. to hydrate the thin lipid membrane, and then add the above described vesicle suspension with a diameter of 50 nm.
- Carry out the same operation as that described in (3) above in the aforementioned hydrophobized glass vessel to hydrate the thin lipid membrane.

Figure 8:
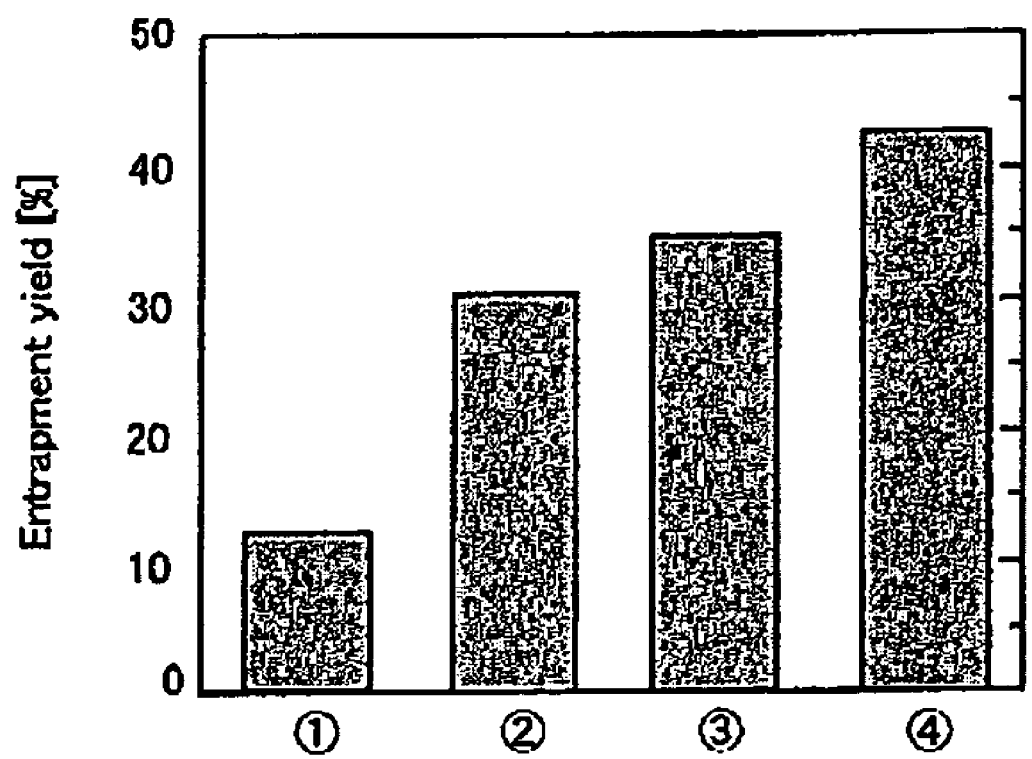
FIG. 8 is a view showing the entrapment yields of calceins in the vesicles produced in Example 2.

The entrapment yields of calceins in the vesicles produced by these treatments are shown in FIG. 8. The numbers (1) to (4) added to the data shown in the figure correspond to the results of the above described operations (1) to (4). As shown in the figure, the entrapment yields of calceins were improved by the aforementioned modifications, and in the method described in (4) above, a high entrapment yield (43%) corresponding to a value 3.6 times higher than the value of Example 1 was achieved.

Example 3

Figure 9:
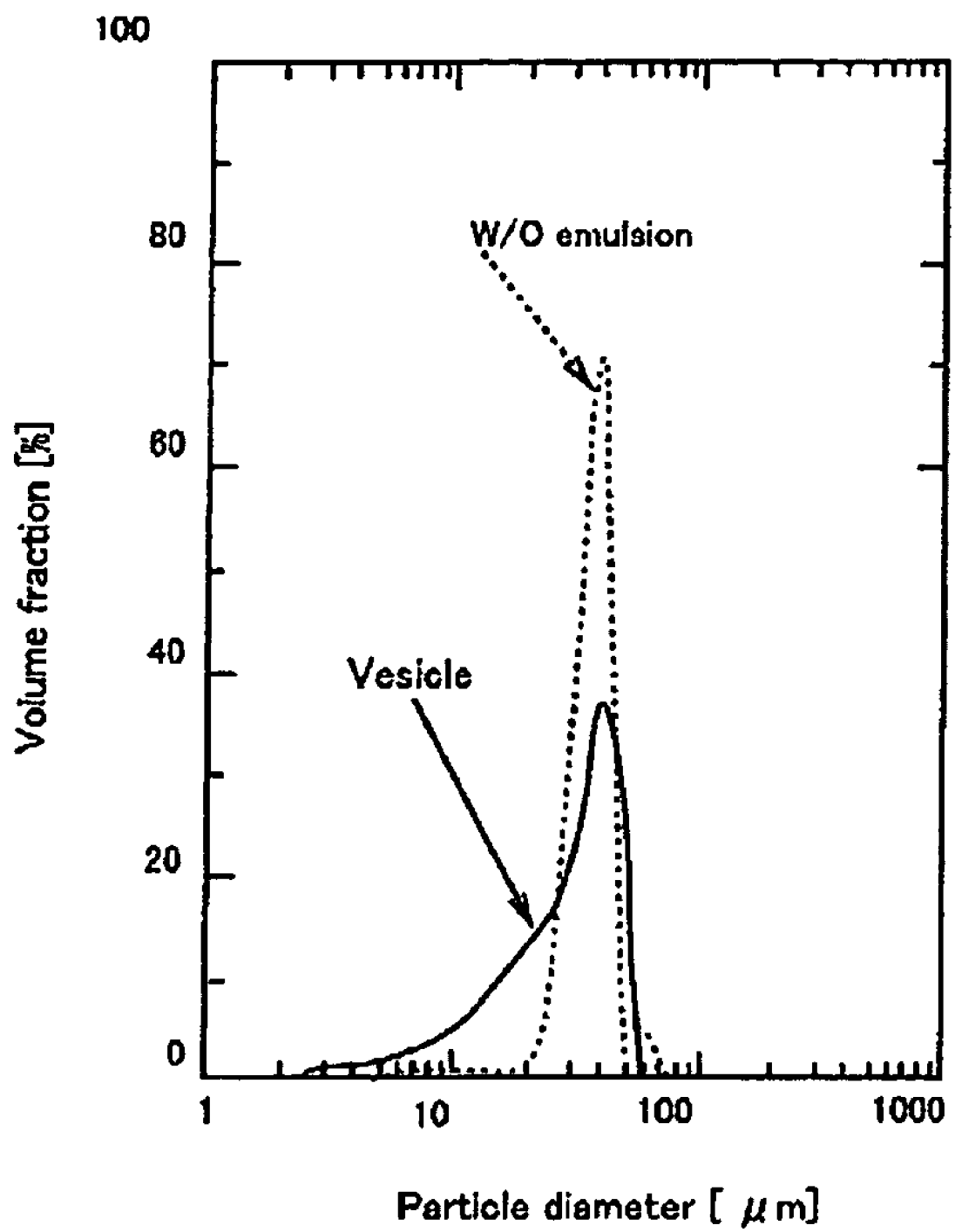
FIG. 9 is a view showing particle diameter distribution of the vesicles produced in Example 3.

As a microchannel substrate used in the production of the W/O emulsion used in Example 1, there was used a microchannel substrate having a terrace length of 30 μm, a channel depth of 11 μm, and a channel width of 16 μm. As a result, a W/O emulsion having a uniform diameter (mean particle diameter: 36 μm) was obtained. Using this emulsion as a base material, a vesicle was produced by the same procedures as those of Example 1. As a result, there could be obtained a vesicle, in which calcein was entrapped and which had a diameter peak at approximately 40 μm (FIG. 9).

That is to say, it was demonstrated that, by the technique of the present invention, a W/O emulsions having different sizes are produced using various types of microchannel substrates, and such emulsions are used as base materials to produce vesicles, so that vesicles having desired sizes can be efficiently produced.

Example 4

As substances to be entrapped in vesicles, polysaccharide dextran (a fluorescently-labeled product; molecular weight: approximately 4,000 to 40,000) and enzyme α-chymotrypsin (molecular weight: 25,310) were used. These entrapped substances were each dissolved in a water phase used in the production of a W/O emulsion by the same procedures as those of Example 1, and vesicles were produced by the same operations as those of Example 1. As a result, a dextran-entrapped vesicle was obtained at an entrapment yield of 6% to 10%, and an α-chymotrypsin-entrapped vesicle was obtained at an entrapment yield of 45%. These results demonstrated that the present invention can be applied not only to the entrapment of calcein, but also to the entrapment of polymeric substances. Moreover, the specific activity of the entrapped α-chymotrypsin was 80% or more of the specific activity before being entrapped. Thus, it could also be confirmed that the present invention relates to a technique of entrapping a biogenic substance such as enzyme in a vesicle, while keeping the activity of the substance high.

Example 5

A vesicle constituent lipid was directly used to produce a W/O emulsion having a uniform diameter, without using a sorbitan fatty acid ester as an emulsifier in the production of such W/O emulsion, so as to improve the efficiency of vesicle production process.

As a microchannel substrate, there was used a microchannel substrate having a terrace length of 20 μm, a channel depth of 2 μm, and a channel width of 10 μm. A cross-flow type microchannel module for experimental use was employed to produce a W/O emulsion in the same manner as that of Example 1. However, as an oil phase, a product obtained by dissolving PC, Chol, and SA in hexane at a molar ratio of 5:5:0 or 5:5:1, resulting in a total lipid concentration of 1.6 to 8 mg/mL, was used. As a water phase, a Tris-HCl buffer solution (50 mmol/L, pH 9) containing 0.4 mmol/L calcein and 0 to 0.5 mol/L NaCl was used.

When a hexane solution containing only PC and Chol was used as an oil phase, W/O emulsion having a uniform diameter could not be obtained. In addition, when lipids in which PC:Chol:SA=5:5:1 were used, if the lipid concentration was 1.3 mg/mL, emulsion having a uniform diameter could not be obtained, as shown in FIG. 10(*a*). However, if the lipid concentration was increased to 6.5 mg/mL in the same above lipid composition, W/O emulsion with a uniform diameter could be obtained, as shown in FIG. 10(*b*).

When NaCl was added into the internal water phase, W/O emulsion with a uniform diameter could be obtained, even though the lipid concentration was lower. The aforementioned results were summarized in Table 1. These results demonstrated that addition of a charged lipid such as SA (50-nm vesicle) and addition of salts such as NaCl are effective for stable production of a W/O emulsion.

TABLE 1

| | | | | |
|---|---|---|---|---|
| Tris-HCl buffer solution | ○ | ○ | ○ | ○ |
| 50-nm vesicle | — | ○ | ○ | ○ |
| Hydration temperature | 4° C. | 4° C. | −2° C. | −2° C. |
| Hydrophobization of glass surface | — | — | — | ○ |

The produced W/O emulsion was frozen in liquid nitrogen, and it was then preserved in a low-temperature chamber at −20° C. By this treatment, emulsion in which the oil phase remained as a liquid and the water phase became a solid could be obtained. After the removal of any given amount of oil phase, hexane containing any given concentration of vesicle constituent lipid was added to the remaining emulsion, so that the water phase concentration and the lipid concentration in the emulsion were adjusted. Thereafter, the hexane was removed at −5° C. to −10° C. and at 15 to 20 hPa in the same manner as that of Example 1. Thereafter, a Tris-HCl buffer solution (50 mmol/L, pH 9) was added to the remaining emulsion at a temperature of 4° C., so as to hydrate a thin lipid membrane that covered the water phase droplet. Thereafter, the same buffer solution was further added thereto to obtain a vesicle suspension. It could be confirmed by observation under a fluorescence microscope that a calcein-entrapped vesicle can be obtained even by these procedures. In this experiment, the entrapment yield of calcein was found to be approximately 18%.

Although there have been described what are the present embodiments of the invention, it will be understood that variations and modifications may be made thereto within the scope of the claims appended hereto.

The invention claimed is:

1. A method for producing a vesicle, which comprises the following steps (1) to (4):
   (1) a step of producing a W/O emulsion from an aqueous solution containing a substance to be entrapped in a vesicle in a dissolved or suspended state and a first oil phase containing an emulsifier;
   (2) a step of cooling the W/O emulsion to a temperature at which the aqueous solution becomes a frozen particle and the oil phase maintains a liquid state, and removing the first oil phase while retaining at least some of the emulsifier on the surface of the frozen particle;
   (3) a step of adding a second oil phase containing a vesicle constituent lipid to the frozen particle and then stirring the mixture, so as to substitute the emulsifier on the surface of the frozen particle with the vesicle constituent lipid, wherein a lipid bilayer membrane is formed on an outer surface of the frozen particle while maintaining an internal water phase in the particle; and
   (4) a step of adding an external water phase to the frozen particle coated with a lipid membrane, so as to hydrate the lipid membrane by the external water phase.

2. A method for producing a vesicle, which comprises the following steps (1) to (3):
   (1) a step of producing a W/O emulsion from an aqueous solution containing a substance to be entrapped in a vesicle in a dissolved or suspended state and an oil phase containing a lipid that functions as an emulsifier;
   (2) a step of cooling the W/O emulsion to a temperature at which the aqueous solution becomes a frozen particle and the oil phase maintains a liquid state, and removing the oil phase in a manner so as to form a lipid bilayer membrane on an outer surface of the frozen particle while maintaining an internal water phase in the particle; and
   (3) a step of adding an external water phase to the frozen particle, so as to hydrate the lipid bilayer membrane by the external water phase on the surface of the frozen particle.

3. The method for producing a vesicle according to claim 1, wherein, when the external water phase is added to the frozen particle, a fine vesicle coated with the same type of lipid membrane is also mixed therein.

4. The method for producing a vesicle according to claim 1, wherein, when the external water phase is added to the frozen particle, a substance for lowering the freezing point of the external water phase is also added thereto.

5. The method for producing a vesicle according to claim 1, wherein the oil phase is removed by evaporation under reduced pressure, and at the time, the inside of a vessel has been hydrophobized.

6. A vesicle produced by the method for producing a vesicle according to claim 1.

7. A method for producing a frozen particle used in the production of a vesicle, which comprises the following steps (1) to (3):
   (1) a step of producing a W/O emulsion from an aqueous solution containing a substance to be entrapped in a vesicle in a dissolved or suspended state and a first oil phase containing an emulsifier;
   (2) a step of cooling the W/O emulsion to a temperature at which the aqueous solution becomes a frozen particle and the oil phase maintains a liquid state, and removing the first oil phase while retaining at least some of the emulsifier on the surface of the frozen particle, wherein said cooling step is performed in a manner so as to form a lipid bilayer membrane on an outer surface of the frozen particle while maintaining an internal water phase in the particle; and
   (3) a step of adding a second oil phase containing a vesicle constituent lipid to the frozen particle and then stirring the mixture, so as to substitute the emulsifier on the surface of the frozen particle with the vesicle constituent lipid.

8. A method for producing a frozen particle used in the production of a vesicle, which comprises the following steps (1) and (2):
   (1) a step of producing a W/O emulsion from an aqueous solution containing a substance to be entrapped in a vesicle in a dissolved or suspended state and an oil phase containing a lipid that functions as an emulsifier; and
   (2) a step of cooling the W/O emulsion to a temperature at which the aqueous solution becomes a frozen particle coated with a lipid membrane and the oil phase maintains a liquid state, and removing the oil phase in a manner so as to form a lipid bilayer membrane on an outer surface of the frozen particle while maintaining an internal water phase in the particle.

9. The method for producing a vesicle according to claim 4 wherein, the substance for lowering the freezing point of the external water phase is glycerol.

10. The method for producing a vesicle according to claim 2 wherein, when the external water phase is added to the frozen particle, a fine vesicle coated with the same type of lipid membrane is also mixed therein.

11. The method for producing a vesicle according to claim 2, wherein, when the external water phase is added to the frozen particle, a substance for lowering the freezing point of the external water phase is also added thereto.

12. The method for producing a vesicle according to claim 11 wherein, the substance for lowering the freezing point of the external water phase is glycerol.

13. The method for producing a vesicle according to claim 2, wherein the oil phase is removed by evaporation under reduced pressure, and at the time, the inside of a vessel has been hydrophobized.

14. A vesicle produced by the method for producing a vesicle according to claim 2.

15. A vesicle produced by the method for producing a vesicle according to claim 3.

16. A vesicle produced by the method for producing a vesicle according to claim 4.

17. A vesicle produced by the method for producing a vesicle according to claim 5.

18. A vesicle produced by the method for producing a vesicle according to claim 10.

19. A vesicle produced by the method for producing a vesicle according to claim 11.

20. A vesicle produced by the method for producing a vesicle according to claim 13.

21. The method of claim 1, wherein the emulsifier is selected from the group consisting of phospholipids, sorbitan fatty acid esters, polyglycerin fatty acid esters, sucrose esters, and mixtures thereof.

22. The method of claim 1, wherein the vesicle constituent lipid comprises a component selected from the group consisting of phospholipids, edible emulsifiers, and fatty acids.

23. The vesicle of claim 6, wherein the vesicle constituent lipid comprises a component selected from the group consisting of phospholipids, edible emulsifiers, and fatty acids.

24. The vesicle of claim 6, wherein the lipid bilayer membrane comprises an additional component selected from the group consisting of sterols, charged lipids, long-chain fatty acids, peptides and carbohydrates.

25. The method of claim 7, further comprising a step of removing the second oil phase by evaporation using an evaporator under reduced pressure while the water phase is kept frozen.

* * * * *